(12) United States Patent
Pratsinis et al.

(10) Patent No.: US 12,196,727 B2
(45) Date of Patent: Jan. 14, 2025

(54) DEVICE AND METHOD FOR DETECTING AN ANALYTE (71) Applicant: ETH Zurich, Zurich (CH)

(72) Inventors: Sotiris Pratsinis, Zürich (CH); Andreas Güntner, Horgen (CH); Jan van den Broek, Zürich (CH); Sebastian Abegg, Zürich (CH)

(73) Assignee: ETH ZURICH, Zurich (CH)

(*) Notice: Subject to any disclaimer, the term of this patent is extended or adjusted under 35 U.S.C. 154(b) by 240 days.

(21) Appl. No.: 17/421,568

(22) PCT Filed: Dec. 20, 2019

(86) PCT No.: PCT/EP2019/086797
§ 371 (c)(1),
(2) Date: Jul. 8, 2021

(87) PCT Pub. No.: WO2020/144059
PCT Pub. Date: Jul. 16, 2020

(65) Prior Publication Data
US 2022/0082541 A1 Mar. 17, 2022

(30) Foreign Application Priority Data
Jan. 11, 2019 (DE) .............. 10 2019 100 587.6

(51) Int. Cl.
G01N 33/00 (2006.01)
A61B 5/08 (2006.01)
G01N 33/497 (2006.01)

(52) U.S. Cl.
CPC ......... *G01N 33/0014* (2013.01); *A61B 5/082* (2013.01); *G01N 33/4972* (2013.01)

(58) Field of Classification Search
CPC .......... G01N 33/0014; G01N 33/4972; G01N 33/497; A61B 5/082
See application file for complete search history.

(56) References Cited

U.S. PATENT DOCUMENTS 5,049,594 A * 9/1991 Jeffs ................... C09C 3/10
524/451
5,457,333 A * 10/1995 Fukui ................. G01N 27/16
257/253

(Continued)

FOREIGN PATENT DOCUMENTS

EP 3346267 A1 7/2018
JP 2008180529 A 8/2008

(Continued)

OTHER PUBLICATIONS

Jan van den Broek, Andreas T. Gantner and Sotiris E Pratsinis, Isoprene Selective Gas Sensing by Adsorption Filter, 2018, DOI 10.5162/IMCS2018/DH2.1 (Year: 2018).*

(Continued)

Primary Examiner — Jennifer Wecker
Assistant Examiner — Ali Husain Faraz
(74) Attorney, Agent, or Firm — Murphy, Bilak & Homiller, PLLC (57) ABSTRACT The invention relates to a device (1) for detecting an analyte in a gas mixture or a liquid, comprising: (a) a polymer sorption filter (2) configured to separate methanol from ethanol; and/or to separate hydrogen and/or methane from interferants; and (b) means configured to detect (4) at least one of methanol, ethanol, hydrogen and methane. Furthermore, described is a method for detecting an analyte using the device and the use of the device.

20 Claims, 4 Drawing Sheets (56) References Cited

U.S. PATENT DOCUMENTS

| | | | |
|---|---|---|---|
| 7,098,253 B2 * | 8/2006 | Rasmussen | B01J 41/20 |
| | | | 526/309 |
| 9,643,186 B1 * | 5/2017 | Ahmad | G01N 33/542 |
| 2005/0090018 A1 | 4/2005 | Walte et al. | |
| 2011/0138881 A1 | 6/2011 | Jones et al. | |

FOREIGN PATENT DOCUMENTS

| | | |
|---|---|---|
| KR | 20150005361 A | 1/2015 |
| WO | 9101001 A1 | 1/1991 |
| WO | 2018017699 A1 | 1/2018 |
| WO | 2018083130 A1 | 5/2018 |

OTHER PUBLICATIONS

"Quintron, Breath Tracker Analyzer", www.breathtests.com/instrumentation, Dec. 18, 2004.

Alfeeli, Bassam, et al., "Evaluation of Tenax TA thin films as adsorbent material for micropreconcentration applications.", Microchemical Journal, vol. 95, 2010, pp. 259-267.

Lonergan, Mark C., et al., "Array-Based Vapor Sensing Using Chemically Sensitive, Carbon Black-Polymer Resistors", Chemistry of Materials, American Chemical Society, vol. 8, Jan. 1, 1996, pp. 2298-2312.

Pennazza, Giorgio, et al., "Measure chain for exhaled breath collection and analysis: A novel approach suitable for frail respiratory patients", Sensors and Actuators B: Chemical, vol. 204, 2014, pp. 578-587.

Van Den Broek, Jan, et al., "Isoprene selective gas sensing by adsorption filter", 17th International meeting on Chemical Sensors—IMCS, 2018, pp. 145-146.

* cited by examiner

DEVICE AND METHOD FOR DETECTING AN ANALYTE

The invention relates to a device and a method for detecting an analyte in a gas mixture or a liquid and the use of the device in this method.

Methanol poisoning from laced liquor leads to blindness, organ failure or death when recognized and treated too late.

Alcohol sensors in general and specifically for breath are available as handheld devices, but they cannot differentiate ethanol from methanol and thus fail to diagnose methanol intoxication.

Therefore, there is the need for a compact detector for quick diagnosis of methanol intoxication or to identify laced beverages, mainly because sensors fail to distinguish methanol from the high ethanol background.

From WO 2018/083130 A1 an analyzer is known for the detection of a target compound in a complex gas mixture in the gas phase, comprising a detector for detecting the target compound and a molecular sieve membrane for separating the target compound. The molecular sieve membrane for separating can be a zeolite, a zeolite imidazolate framework, a metal organic framework, a carbon molecular sieve or a zeolitic MFI layer on alumina. The analyzer is based on a physical size cut off, but sorption effects are not disclosed.

Furthermore, hydrogen and methane in the breathing air are associated with intestinal disorders, for example lactose intolerance. The gold standard used in hospital for diagnosis of intestinal disorders is a device based on a mini-GC coupled with a solid-state gas sensor capable to selectively detect $CH_4$ and $H_2$ (Quintron, *Breath Tracker Analyzer*, 18/12/04, www.breathtests.com/instrumentation). This device is expensive, not handheld and has only a low accuracy (5% or 3 ppm).

Therefore, the technical problem underlying the present invention is to provide a device and a method for selectively and reliably detecting an analyte in a gas mixture or a liquid, wherein the device can be miniaturized to be compact so that it can be held in one hand of a human being.

This is achieved by the device of claim 1, the method of claim 15 and the use of claim 19. Preferred embodiments are defined in the dependent claims.

The device according to the present invention for detecting an analyte in a gas mixture or a liquid comprises
- (a) a polymer sorption filter configured to separate methanol from ethanol; and/or to separate hydrogen and/or methane from interferants for example in gas mixtures (e.g. breathing air); and
- (b) means configured to detect at least one of methanol, ethanol, hydrogen and methane.

The polymer sorption filter can be an adsorption filter and/or an absorption filter.

An analyte in the sense of the present invention is any compound to be analyzed, for example a gaseous compound, like methanol, ethanol, hydrogen and methane.

A gas mixture in the sense of the present invention refers to a gaseous mixture containing the analyte together with at least one further gaseous compound. Examples are breathing air; the headspace of a liquid or solid containing the analyte; and a liquid or solid that is at least partially transformed into a gaseous state, for instance by the means of heating.

The interferant in the sense of the present invention is any further compound present in the gas mixture or the liquid together with the analyte, which can interfere with the analysis of the analyte. Such interferants can be an alcohol like ethanol, ketones, ammonia and hydrocarbons (other than methane).

With the device according to the present invention, methanol in the gas phase can be separated from ethanol and other interferants by the polymer sorption filter which ad- and/or absorbs ethanol stronger than methanol. The separated methanol is then detected separately without interference by the above means for detecting. If required, this can be an array of different means.

Further, with the device according to the present invention, hydrogen and methane in the gas phase can be separated from interferants in gas mixtures, like ketones, ammonia, alcohols and hydrocarbons (others than methane) by the polymer sorption filter, which adsorbs and retains the interferants, while hydrogen and methane are not affected as strong. The separated hydrogen and methane can be detected by the means for detecting. If required, this can be an array of different means.

The device according to the present invention is a portable, inexpensive, fast, selective and reliable detector for an analyte, like methanol in human breath air and beverages as well as hydrogen and methane in breath air. It can be held and carried in one hand of a user/human being. The analytes, in particular methanol, can be detected within about 2.5 minutes down to about 100 ppb independent of the interfering ethanol concentration. The device can therefore be suitably used for fast screening of methanol poisoning by first-responder or in the hospital and help to prevent outbreaks by direct testing of beverages. The device can be used for the diagnosis of methanol intoxication and monitoring of its treatment from breath and for detection of methanol-laced alcohol by testing their headspace (the gas immediately above the liquid) or transforming the liquid at least partially into a gaseous state. In the case of hydrogen and methane detection, the device can be used for the diagnosis of intestinal disorders associated with hydrogen and methane in the breathing air, like lactose intolerance, as well as for individual monitoring of patients.

In one embodiment, the device according to the present invention is configured so that it can be held in one hand of a user/human being. This can be achieved by selecting the means for separating and the means for detecting in such a way that the whole device can be held by one hand. For example the length of the device is about 20 cm or less, for example about 15 cm or less or about 10 cm or less. Furthermore, the width of the device can be about 8 cm or less, for example about 7 cm or less or about 5 cm or less. With these dimensions, a particular useful device to be held in one hand can be obtained.

In the device according to the present invention, a means for separating is used. Separation can take place by sorption on a polymer sorption filter with a sorption capacity and/or sorption strength to sorb the present methanol and ethanol. The difference in the sorption capacity and/or sorption strength is such that methanol and ethanol can be separated from each other. In case of separation of hydrogen and methane, separation can take place as well by sorption on a polymer sorption filter as mentioned above. The means for separation has a higher sorption capacity and/or sorption strength to the interferants possibly present in the gas mixture, like ketones, ammonia, alcohols and hydrocarbons with more than 2 carbon atoms or more, than for hydrogen and/or methane.

In one embodiment, the polymer sorption filter is selected from the group consisting of nanoparticles (having a size of 1 nm to 100 nm), microparticles (having a size larger than 100 nm), non-porous and porous materials, in particular microporous materials (pores size 2 nm and less), mesoporous materials (pore size between 2 and 50 nm) and macroporous materials (pores size 50 nm and larger), for example macroporous material having a pore size of 50 nm to 1 µm, for example 100 nm to 300 nm, for instance about 200 nm.

To sufficiently sorb ethanol even at very high concentration at small filter size, the polymer sorbent should have a high specific surface area. This can be achieved by small nanoparticles or by porous materials.

The sorbent also should show a sufficient difference in the sorption capacity and/or sorption strength for methanol and ethanol to separate them. Sorption happens due to electrostatic interaction, hydrogen bonding and/or van der Waals forces. As methanol and ethanol have the same alcohol functional group and only differ by the length of their carbon chain, they both do not show any electrostatic interactions with the sorbent and also hydrogen bonding strength is very similar. Methanol, however, shows generally lower van der Waals sorption forces in comparison to ethanol independent of the specific sorbent based on the lower molecular weight.

In one embodiment, the polymer sorption filter comprises a polymer, selected from the group consisting of polymers with phenyl groups for example polystyrenes, like polystyrene, polyvinylbenzene, and polyethylvinylbenzene; polyethers, like polyphenylethers, for example poly(2,6-diphenylphenylene)oxide; acrylates, like methacrylates; polyamines, like polyethyleneimines; polynitryles, like polyacrylonitriles; poly(vinylpyridine); polyvinylpyrrolidone, and polysiloxanes.

By using polyphenylether, for example poly(2,6-diphenylphenylene)oxide, a particular good separation of methanol and ethanol is achieved. Poly(2,6-diphenylphenylene) oxide is commercially available as Tenax TA. From this compound it is known that volatile compounds like ethanol, acetone and 2-propanol are not sufficiently retained (see www.dguv.de/ifa/forschung/projektverzeichnis/bgia 2066.isp). In the light of this finding, it was surprising that polymer sorption filters can be used to separate methanol from ethanol in that ethanol is retained sufficiently longer than methanol.

Homo- and/or copolymers of the above polymers can be used.

In a further embodiment, the polymer sorption filter is configured as a packed bed of particles; as a coating; as a membrane; as a foam structure; or as an overlayer applied onto the means configured to detect at least one of methanol, ethanol, hydrogen and methane. The filter can be arranged as a dead-end configuration, i.e. the sensor is placed in a cavity that is closed by the filter, or in an open-end configuration, i.e. the gas can enter through an inlet (that might comprise the filter) and exit by an outlet, therefore allowing an active flow through the filter. With these configurations it is possible to obtain a good separation of methanol and ethanol. Furthermore, these configurations are very suitable for miniaturizing the device so that a very compact device can be obtained which can be easily held in the hand of a user/human being.

In a further embodiment, the polymer sorption filter can meet at least one of the following parameters independently:
  Weight of filter material: It can be smaller than about 10 g, in particular smaller than about 5 g, in particular smaller than about 1 g, for example smaller than about 500 mg, for instance 100 mg to 300 mg, like about 250 mg.
  Filter surface: The specific surface area of the filter can be larger than about 5 $m^2/g$, for example larger than about 10 $m^2/g$, like larger than about 20 $m^2/g$, for example about 35 $m^2/g$. The surface is measured by BET nitrogen adsorption.
  Temperature: The filter can be operated at a temperature below about 200° C., for example below about 100° C., below about 80° C., below about 50° C., for example at about room temperature. The device according to the present invention can be configured by respective cooling means and/or heating means to provide the temperature, as far as necessary. The operating temperature of the means configured to detect the analyte can be different from the above operating temperature of the filler depending on the kind of detector used.
  Cross-sectional area: The filter housing can have a cross-sectional area smaller than about 350 $mm^2$, for example smaller than about 100 $mm^2$, smaller than about 20 $mm^2$, for example about 12 $mm^2$. The lower value of the cross-sectional area is chosen so that the gas/liquid can sufficiently pass through the filter.
  Filter length: The filter can have a length smaller than about 20 cm, smaller than about 10 cm, smaller than about 5 cm, for example about 3 cm.

It has been advantageously found that with the above parameters it is possible to provide a particular useful miniaturization of the device so that a very compact device can be obtained, which can be easily held in one hand of a human being.

The sensors (i.e. means configured to detect the particular analyte) that can be generally used as means for detection are sensors which can fit into a handheld device and detect the target analyte in the relevant concentrations, for example sensors of resistive type like chemo-resistive metal oxides, ion conductors, polymers, carbon nanotubes, or graphene; of amperometric type like electrochemical sensors; of capacitive type; of potentiometric type; of optical type; of thermal type; of thermochemical type; of thermophysical type; of gravimetric type; of biochemical type or any combination thereof.

In another embodiment, the means configured to detect at least one of methanol, ethanol, hydrogen and methane is a metal oxide gas sensor, for example selected from the group consisting of
  $SnO_2$, in particular doped $SnO_2$ (e.g. 1 mol % Pd-, 6 mol % Si-, 0.15 mol % Pt- or 4.6 mol % Ti-doped);
  $WO_3$, in particular doped $WO_3$ (e.g. 10 mol % Si-, or 10 at % Cr-doped);
  ZnO, in particular doped ZnO (e.g. 2.5 mol % Ti-doped);
  $MoO_3$, in particular doped $MoO_3$ (e.g. 3 wt. % Si-doped);
  $In_2O_3$, in particular doped $In_2O_3$; and
  $TiO_2$, in particular doped $TiO_2$.

Metal-oxide sensors offer a simple application, high miniaturization potential, low power consumption and minimal production costs. The mechanism relies on changes of electrical conductivity by the change in the surrounding atmosphere. Gas detection is related to the reactions between ionosorbed surface oxygen and target analyte gas (receptor function). The equilibrium state of the surface oxygen reaction is shifted by the target analyte (receptor function) changing the sensing material's resistance (transducer function).

Further provided is a method for detecting an analyte in a gas mixture or a liquid, wherein the gas mixture or the liquid is analyzed by the device according to the present invention as described above in detail in order to detect the analyte. The detailed process steps as far as not explicitly indicated can be taken from the configuration of the device.

In one embodiment, the gas mixture to be analyzed comprises breathing air; the headspace of a liquid or solid; or of an at least partially evaporated liquid or solid. The analyte to be analyzed can be methanol, ethanol, hydrogen, methane and mixtures thereof, for example a mixture containing methanol and ethanol, or a mixture containing hydrogen and methane together with interferants, like ketones, ammonia, alcohols and hydrocarbons (others than methane), wherein the analyte is present in the gas mixture, the liquid or solid.

The method according to the present invention can be carried out in 30 minutes or less, in particular 15 min or less, in particular 10 min or less, in particular 5 min or less, for example 2.5 minutes or less. Furthermore, the method can detect the analyte in amounts down 10 ppm, in particular down to 5 ppm, in particular down to 1 ppm, for example down to 100 ppb.

Furthermore, the present invention relates to the use of the above device according to the present invention for detecting at least one of methanol, ethanol, hydrogen or methane, in particular in a gas mixture (e.g. breathing air); in a liquid; in the headspace of a liquid or solid; or in at least partially evaporated liquids or solids. In case of the detection of methanol, the use according to the present invention envisages the diagnosis of methanol intoxication, the detection of the content of methanol in a beverage or gas as well as the monitoring of the therapy of the methanol intoxication. In case of the detection of hydrogen and methane, the use according to the present invention can be applied to the diagnosis of intestinal disorders and the monitoring of the therapy of such intestinal disorders.

The device may be equipped for medical and biological fluid analysis, in particular breath analysis, analysis of skin emissions, headspace analysis of fluids. The device may be a breath detector, skin analyser, headspace analyser for fluids. Furthermore, the device may be equipped for food processing control, food quality assessment monitoring of agricultural processes and products, monitoring and control of chemical processes, indoor air analysis, environmental analysis, detection of explosives and other hazardous compounds, exhaust emission monitoring and control and/or air quality analysis. The device may be a food processing analyser, food quality analyser and/or an air quality analyser. Accordingly, the detection of a target compound originating from a medical or biological fluid for example in breath, from skin emissions, during food processing, in food or air is enabled. In the headspace analysis and respectively other analyses of fluids only the gas phase above the fluid is analysed, accordingly it might be called a (headspace) analysis of fluids in the gas phase.

The present invention is further described by the following figures and examples. It is to be noted that the figures and the examples are only intended for illustrating the invention but not to restrict the invention thereto.

FIG. 1a, b shows the device according to the present invention.

FIG. 3a,b shows the response of a Pd-doped $SnO_2$ sensor with a polymer sorption filter to various analytes.

FIG. 4a,b shows the relationship of the sensor response at different methanol concentrations.

FIG. 6a,b shows the response a Pd-doped $SnO_2$ sensor with a polymer sorption filter when sampling breath of a sober (FIG. 6a) and a drunken person (FIG. 6b).

In FIG. 1a, the device 1 according to the present invention is schematically shown for the example of an open-end configuration. The device contains a polymer sorption filter 2 which is connected by connection 3 with the means configured to detect 4. The polymer sorption filter 2 is connected with an inlet 7 for guiding the gas mixture into the polymer sorption filter 2. An example for the inlet 7 can be a mouth pipe for analyzing the breathing air. Furthermore, the means configured to detect 4 is connected by connection 5 with a pump 6 (optional) for pumping the gas mixture through the device if necessary. The detection of methanol poisoning in breathing air and spirits is carried out with the device 1 as follows. Breath or the headspace of a beverage is sampled by the pump 6 through the polymer sorption filter 2 to the means configured to detect 4. The polymer sorption filter 2 retains ethanol more strongly than methanol which is detected by the means for detecting 4 without interference within about 2 minutes.

Figure 1:
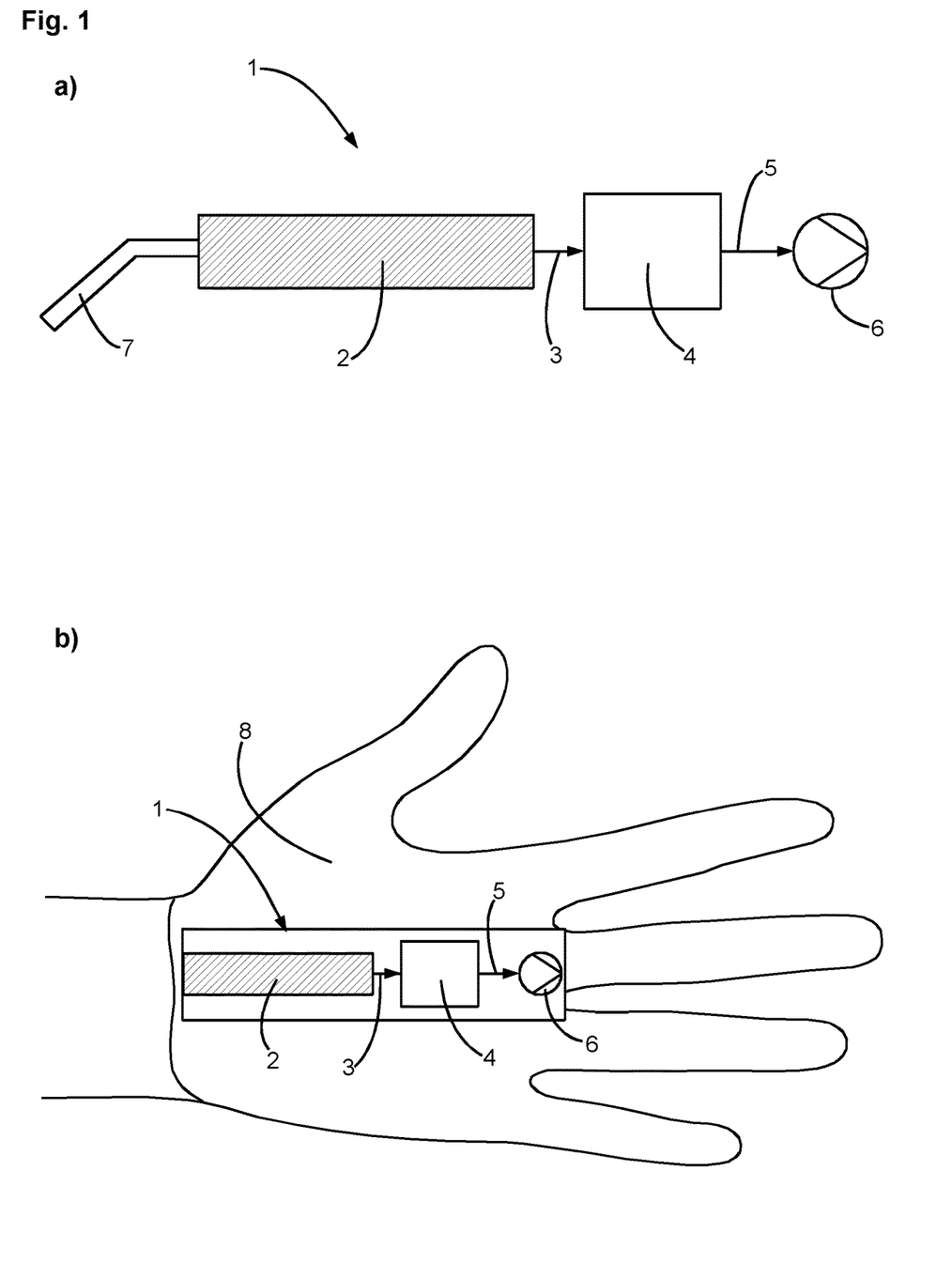

In FIG. 1b, the device of FIG. 1 is shown in relation to the hand 8 of a human being. This figure shows that the device according to the present invention can be miniaturized in such a small and compact way that it can be held in one hand of a human being.

Figure 2:
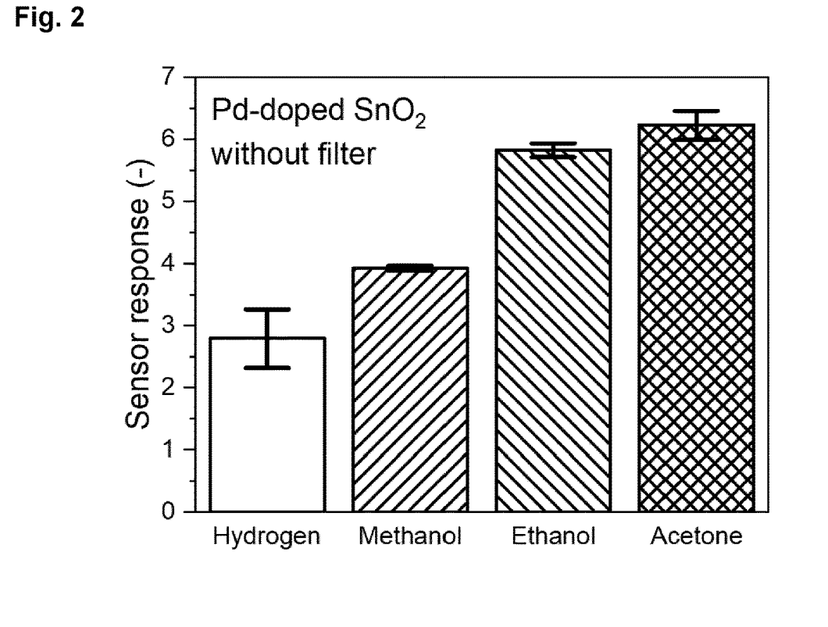
FIG. 2 shows the response of a Pd-doped $SnO_2$ sensor to various analytes.

FIG. 2 shows the responses of a Pd-doped $SnO_2$ sensor without filter to 1 ppm of hydrogen, methanol, ethanol and acetone. The sensor is operated at 370° C. in a continuous flow of 25 ml/min synthetic air at 50% relative humidity. It can be taken from the results that each of hydrogen, methanol, ethanol and acetone can be detected by the used sensor, however, only in single gas mixtures, i.e. without interference. Thus, the sensor without filter is not able to distinguish, for instance, methanol from ethanol.

Figure 3:
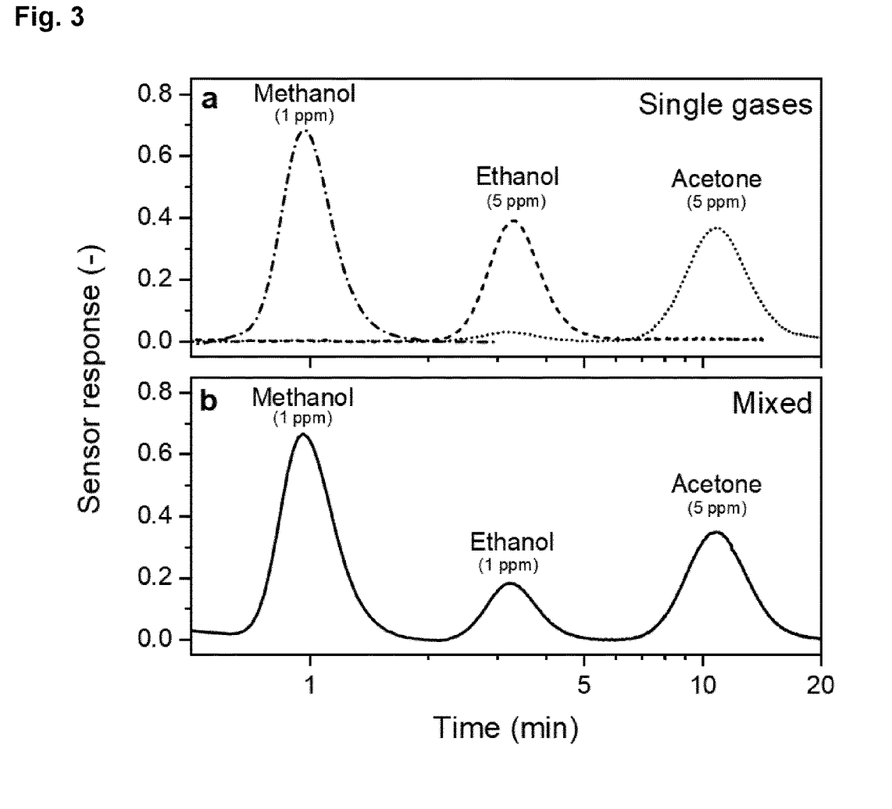

In FIG. 3a the response is shown of a Pd-doped $SnO_2$ sensor with filter (100 mg porous poly(2,6-diphenylphenylene)oxide (Tenax TA) as porous polymer sorption filter, length is about 3 cm, cross section is 13 mm$^2$, surface is 35 m$^2$/g, operated at room temperature) to 10 s pulses of methanol (dash/dotted line), ethanol (dashed line) and acetone (dotted line) in a continuous flow of 50 ml/min synthetic air at 50% relative humidity. When exposing the sensor to a mixture of the same analytes, it detects each individually as they are completely separated by the filter as can be taken from FIG. 3b.

Figure 4:
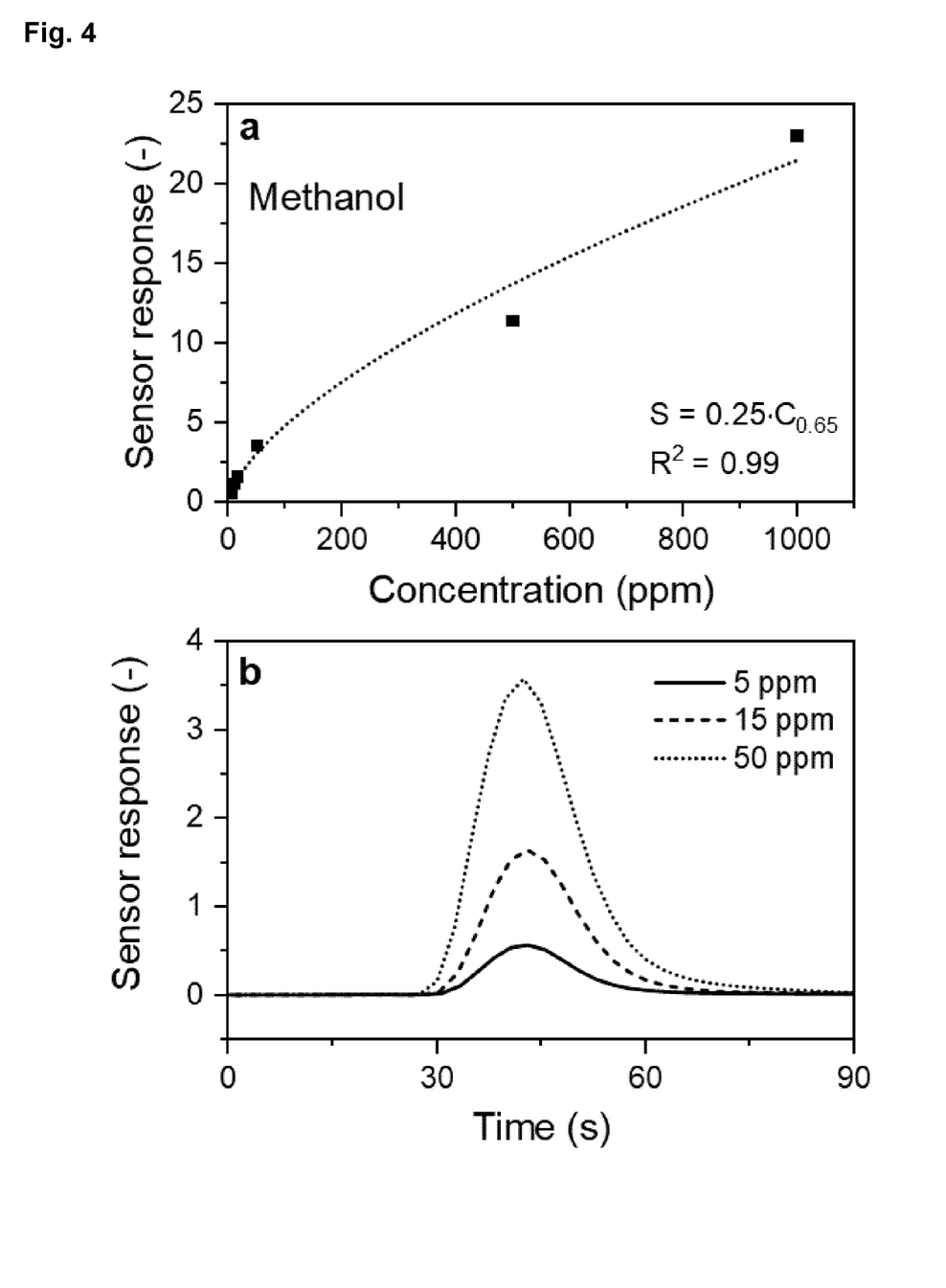

FIG. 4a shows the responses of a Pd-doped $SnO_2$ sensor with filter (300 mg porous poly(2,6-diphenylphenylene) oxide (Tenax TA) as porous polymer sorption filter) when sampling methanol concentrations in the range 5-1000 ppm. Sensor response curves to low concentrations of methanol of 5 (solid line), 15 (dashed line) and 50 ppm (dotted line) is shown in FIG. 4b. Even these low but breath-relevant concentrations can be detected and are clearly distinguishable. Air was sampled continuously at 100 ml/min through the filter to the sensor by a pump. Samples were drawn for 10 s from Tedlar bags where the desired concentration of methanol was admixed with synthetic air at 50% relative humidity.

Figure 5:
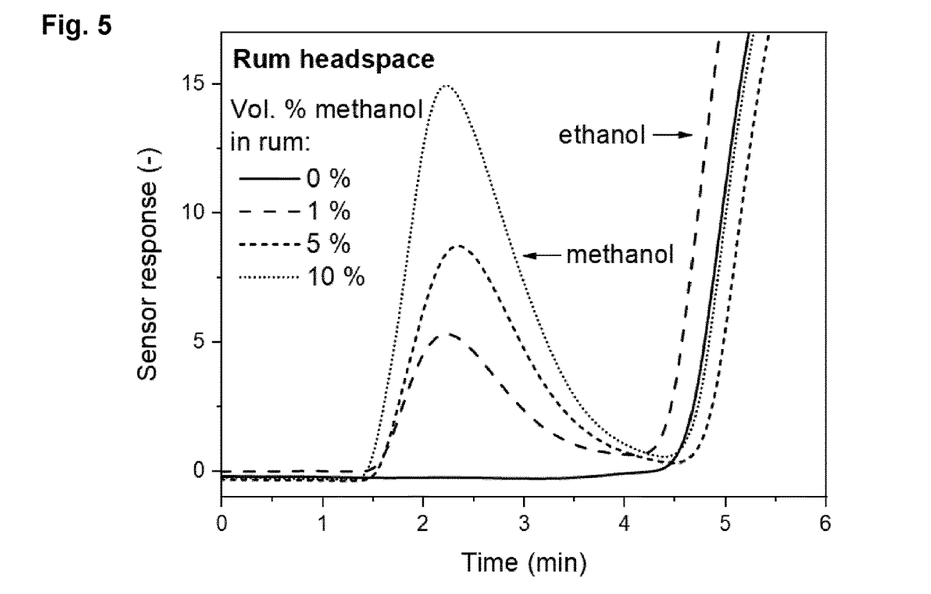
FIG. 5 shows the response of a Pd-doped $SnO_2$ sensor with a polymer sorption filter when sampling the headspace of rum with different amounts of methanol.

In FIG. 5 the response of a Pd-doped $SnO_2$ sensor is represented with filter (150 mg porous poly(2,6-diphenylphenylene)oxide (Tenax TA) as porous polymer sorption filter) when sampling for 5 s in the headspace of a rum (40 vol. %) that was spiked with different amounts of methanol. Air was sampled continuously with 25 ml/min through the filter to the sensor with a pump. In all cases, the filter fully separates methanol from the high ethanol background and the sensor clearly distinguishes the samples containing toxic amount of methanol from the one without.

Figure 6:
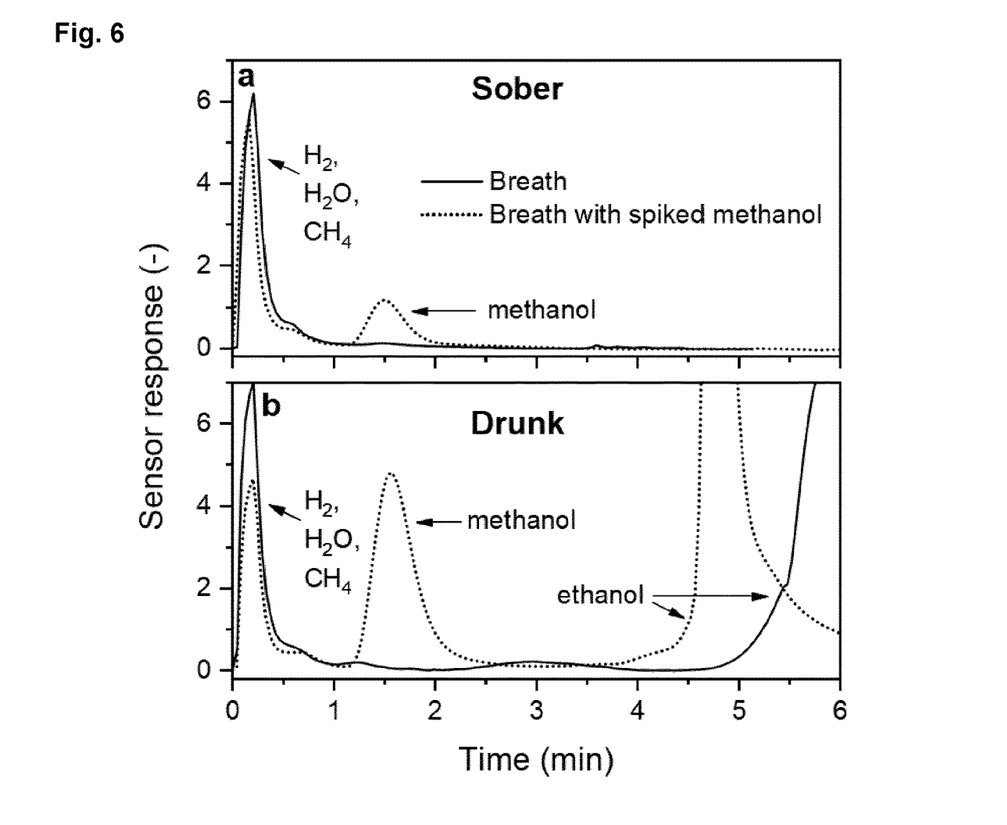

FIG. 6a and FIG. 6b show the response of a Pd-doped $SnO_2$ sensor with filter (300 mg porous poly(2,6-diphenylphenylene)oxide (Tenax TA) as porous polymer sorption filter) when sampling breath of a (FIG. 6a) sober and (FIG. 6b) drunken person from a Tedlar bag for 5 sec. In both cases breath is sampled twice once analyzed as is (solid lines) and once after adding toxic concentrations of methanol (dotted lines). Air was sampled continuously with 50 ml/min through the filter to the sensor with a pump. The sensor completely separates methanol from hydrogen, methane, water and ethanol in the breath and clearly detects the toxic methanol concentration in the spiked samples.

The invention claimed is:

1. A device for detecting an analyte in a gas mixture or a liquid, the device comprising:
a polymer sorption filter configured to separate methanol from ethanol; an inlet and an outlet configured to allow an active flow through the polymer sorption filter;
and one or more sensors configured to detect methanol and/or ethanol in 15 minutes or less,
wherein the polymer sorption filter comprises a packed bed of particles and is configured to retain ethanol longer than methanol,
wherein the polymer sorption filter comprises a polymer selected from the group consisting of polymers with phenyl groups, polyethers, acrylates, polyamines, polynitryles, poly(vinylpyridine), polyvinylpyrrolidone and polysiloxanes,
wherein the one or more sensors are configured to detect a peak maximum of methanol in 10 minutes or less and a peak maximum of ethanol not before 1 minute,
wherein the peak maximum of ethanol is configured to be detected later than the peak maximum of methanol without interference of the peaks.

2. The device of claim 1, wherein the gas mixture comprises breath, a headspace of a liquid and/or solid, or a liquid or solid that is at least partially transformed into a gaseous state.

3. The device of claim 1, wherein the device is configured to be held in a hand of a user.

4. The device of claim 1, wherein the device has a length of 20 cm or less and a width of 8 cm or less.

5. The device of claim 1, wherein the polymer sorption filter comprises nanoparticles and/or microparticles.

6. The device of claim 1, wherein the polymer with phenylgroups is a polyphenylether.

7. The device of claim 6, wherein the polyphenylether is poly (2,6-diphenylphenylene) oxide.

8. The device of claim 1, wherein the polymer sorption filter is present in an amount of 10 g or less.

9. The device of claim 1, wherein the polymer sorption filter has a specific surface area measured by BET nitrogen adsorption of 5 $m^2/g$ or more.

10. The device of claim 1, wherein a housing containing the polymer sorption filter has a cross-sectional area of 350 $mm^2$ or less.

11. The device of claim 1, wherein the polymer sorption filter has a length of 20 cm or less.

12. The device of claim 1, wherein the polymer sorption filter is configured to be operated at a temperature of 200° C. or less.

13. The device of claim 1, wherein the one or more sensors configured to detect methanol and/or ethanol includes a metal oxide gas sensor.

14. The device of claim 13, wherein the metal oxide gas sensor is selected from the group consisting of: an $SnO_2$ sensor; a doped $SnO_2$ sensor; a $WO_3$ sensor; a doped $WO_3$ sensor; a ZnO sensor; a doped ZnO sensor; an $MoO_3$ sensor; a doped $MoO_3$ sensor; an $In_2O_3$ sensor; a doped $In_2O_3$ sensor; a $TiO_2$ sensor; and a doped $TiO_2$ sensor.

15. A method for detecting an analyte in a gas mixture or a liquid using a device, the method comprising:
separating methanol from ethanol by a polymer sorption filter of the device, wherein the polymer sorption filter comprises a packed bed of particles and is configured to retain ethanol longer than methanol, wherein the polymer sorption filter comprises a polymer selected from the group consisting of polymers with phenyl groups, polyethers, acrylates, polyamines, polynitryles, poly (vinylpyridine), polyvinylpyrrolidone and polysiloxanes;
allowing an active flow through the polymer sorption filter via an inlet and an outlet of the device;
detecting methanol and/or ethanol by the device in 15 minutes or less; and
analyzing the gas or the liquid mixture by the device,
wherein the detecting comprises detecting a peak maximum of methanol in 10 minutes or less and a peak maximum of ethanol not before 1 minute,
wherein the peak maximum of ethanol is detected later than the peak maximum of methanol without interference of the peaks.

16. The method of claim 15, wherein the gas mixture comprises breathing air, a headspace of a liquid or solid, or a gaseous state of a liquid or solid that is at least partially transformed into the gaseous state.

17. The method of claim 15, wherein the polymer sorption filter is operated at a temperature of 200° C. or less.

18. A method of using a device configured to detect an analyte in a gas mixture or a liquid, the method comprising:
separating methanol from ethanol by a polymer sorption filter of the device, wherein the polymer sorption filter comprises a packed bed of particles and is configured to retain ethanol longer than methanol, wherein the polymer sorption filter comprises a polymer selected from the group consisting of polymers with phenyl groups, polyethers, acrylates, polyamines, polynitryles, poly (vinylpyridine), polyvinylpyrrolidone and polysiloxanes;
allowing an active flow through the polymer sorption filter via an inlet and an outlet of the device; and
detecting methanol and/or ethanol by the device in 15 minutes or less, in breathing air, in a liquid, in a liquid or solid that is at least partially transformed into a gaseous state, or in a head space of a liquid,
wherein the detecting comprises detecting a peak maximum of methanol in 10 minutes or less and a peak maximum of ethanol not before 1 minute,
wherein the peak maximum of ethanol is detected later than the peak maximum of methanol without interference of the peaks.

19. The device of claim 1, wherein the one or more sensors configured to detect methanol and/or ethanol includes a resistive type sensor, an amperometric type sensor, a capacitive type sensor, a potentiometric type sensor, an optical type sensor, a thermal type sensor, a thermochemical type sensor, a thermophysical type sensor, a gravimetric type sensor, a biochemical type sensor, or any combination thereof.

20. The device of claim 1, wherein the polymer sorption filter is configured to retain ethanol for more than 2 minutes and retain methanol for less than 2 minutes.

* * * * *